United States Patent [19]

Brown

[11] Patent Number: 5,798,116
[45] Date of Patent: Aug. 25, 1998

[54] STABILIZED MATERIALS COMPRISED OF COPPER ION-CONTAINING FIBRONECTIN MATS

[75] Inventor: Robert A. Brown, London, United Kingdom

[73] Assignee: University College London, London, England

[21] Appl. No.: 591,443

[22] PCT Filed: Jul. 29, 1994

[86] PCT No.: PCT/GB94/01648

§ 371 Date: Apr. 17, 1996

§ 102(e) Date: Apr. 17, 1996

[87] PCT Pub. No.: WO95/04078

PCT Pub. Date: Feb. 9, 1995

[30] Foreign Application Priority Data

Jul. 30, 1993 [GB] United Kingdom ............... 9315810

[51] Int. Cl.⁶ .................. A61K 33/34; A61K 9/70; A61L 25/00; A61L 15/00
[52] U.S. Cl. .................. 424/445; 424/630; 606/151; 606/152; 514/8
[58] Field of Search .............. 424/445; 606/214, 606/151, 152

[56] References Cited

U.S. PATENT DOCUMENTS 5,443,816  8/1995  Zamora et al. ............... 424/1.69
5,554,375  9/1996  Pickart ......................... 424/401

FOREIGN PATENT DOCUMENTS 4127790   2/1993  Germany.
91 11206  8/1991  WIPO.
93 13003  8/1992  WIPO.

OTHER PUBLICATIONS

Maquart, et al: "In Vivo Stimulation of Connective Tissue Accumulation by the Tripepetide-Copper Complex Glycyl-L-histidyl-L-$Cu^{2+}$ in Rat Experimental Wounds", The Journal of Clinical Investigation, vol. 92, No. 5, Nov. 1993, pp. 2368–2376, see the whole docoument.

Primary Examiner—Peter F. Kulkosky
Attorney, Agent, or Firm—Pillsbury Madison & Sutro LLP

[57] ABSTRACT

The invention concerns a complex comprising a cell adhesion protein or a fragment thereof and Cu ions. The cell adhesion protein may be, for example, fibronectin and the Cu ions may be, for example, $Cu^{2+}$ ions. The Cu ions stabilize the cell adhesion protein and the complex may be used to promote wound healing.

13 Claims, 3 Drawing Sheets

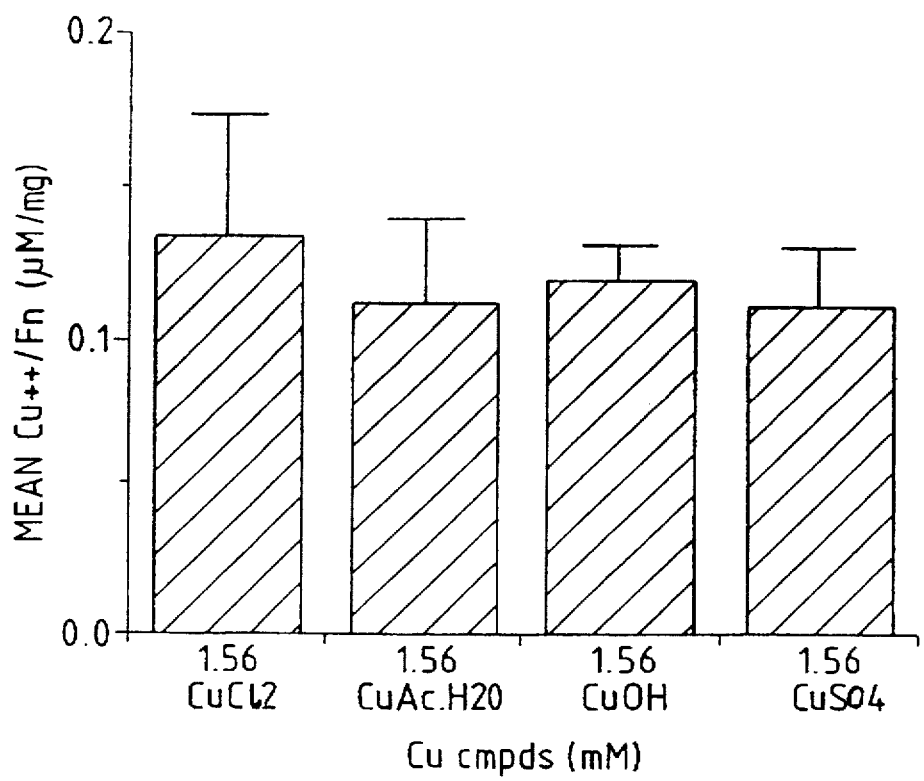

STABILIZED MATERIALS COMPRISED OF COPPER ION-CONTAINING FIBRONECTIN MATS

This application claims benefit of international application PCT/GB94/01648, filed Jul. 29, 1994.

The present invention relates to stabilised materials for wound healing in humans and animals.

There are four stages which can usually be identified in the natural healing process. Initially the wound is closed so as to limit blood loss and prevent infection. Then damaged tissue is removed and pathogens destroyed by phagocytosis. This is followed by granulation in which the wound is invaded by cell types appropriate to the surrounding tissue and scar formation occurs. Finally the scar tissue is remodelled and changes in the cell population occur resulting in a mature, healed wound. In any particular case variations from this general pattern will occur owing to factors such as the site and type of wound and the condition of the patient. The details of the process, particularly the later stages are, as yet, not well understood.

Although very effective in most cases, the natural wound healing process can fail on occasion, or may be unsatisfactory, and medical intervention is desirable. Typical examples of failure include cases of severe burns involving substantial tissue damage where the wounds often do not even close completely and where skin grafts are required to secure granulation, cases of leg ulcers where, even when the wounds heal, the healed scar is physically weak and liable to break open very easily and cases where, although a wound would heal naturally, the scarring that remains may be unsightly or cause discomfort. Other wounds which frequently require intervention are serious bone fractures and wounds to cartilage, ligaments and tendons which heal slowly or not at all or where the healed wound will not be sufficiently strong.

Despite considerable work over many years there have been no completely satisfactory treatments for many of these problems in wound healing. One approach to improving wound healing is the administration of wound healing promoters such as growth factors. However, there are many difficulties with this, particularly in ensuring that the agents are delivered to the site of the wound in effective amounts.

WO-A-9 220 716 describes ferric hyaluronates, which are said to be antimicrobial agents and wound healing agents. They are also said to be useful as carriers for other therapeutically active substances such as TNF, insulin and interferon.

We have previously shown that cell adhesion proteins promote wound healing when applied to the wound and have developed macroscopically oriented materials (WO-A-92/13003), comprising a cell adhesion protein such as fibronectin, which promote wound healing, in particular by creating a scaffolding to which the invading cells can adhere thus facilitating this stage of the wound healing procedure. By aligning these materials with features of the wound or surrounding tissue, cell invasion may be directed along desired orientations thereby strengthening the initial repair and reducing the amount of reorientation required during the remodelling stage. Thus, wound healing may be promoted and the mature healed wound can be made stronger or more cosmetically acceptable or both.

We have also previously developed a depot composition for treatment of wounds comprising fibronectin or a fragment thereof, a growth factor binding agent linked thereto and a growth factor bound to the binding agent (WO-A-92/12739). The growth factor which promotes wound healing is concentrated on and released from an appropriate binding molecule itself immobilised on a material comprising a binding domain of fibronectin.

Copper is known to be important in tissue repair with roles in collagen synthesis (Siegel (1979) Int. Rev. Conn. Tiss. Res. 8, 79–118), free radical clearance (Dogan et al (1989) British Journal of Dermatology (1989) 120, 239–244) and angiogenesis (Brem et al (1990) American Journal of Pathology 137, (5), 1121; Brem et al (1990) Neurosurgery 26, (3), 391; McAuslan and Reilly (1980) Experimental Cell Research 130, 147–157). Copper depletion has been reported in severe wounds/burns and this may influence repair. Copper sulphate can be applied directly to wounds in order to destroy and remove granulation tissue. The aim of this treatment is to control or reduce wound contraction.

We have unexpectedly found that Cu ions are avidly taken up by cell adhesion proteins and that this surprisingly increases the stability of the proteins (possibly by cross-linking them), for example against protease digestion. In addition, the Cu/protein complexes promote wound healing.

Accordingly, the present invention provides a complex comprising a cell adhesion protein or a fragment thereof and Cu ions. The protein or fragment thereof may be fibronectin, vitronectin, von Willebrand protein, laminin, or a fragment thereof. Fibronectin is preferred. The Cu ions may be $Cu^+$ or $Cu^{2+}$ ions.

The term "fragment" is used herein to refer to a portion of a cell adhesion protein capable of promoting wound healing. A fragment generally comprises at least one domain of the cell adhesion protein, preferably a cell adhesion domain. Fibronectin is made up of a number of domains, including the gelatin-binding (cell adhesion) domain, the heparin-binding domain and the cell-binding domain. When a fragment of fibronectin is used, it preferably comprises at least one of the foregoing domains.

A fragment of a cell adhesion protein may be obtained by a conventional method, such as enzymatic cleavage of the protein, synthesis from single amino acids and/or preformed peptides of two or more amino acids, or production using recombinant DNA techniques.

According to a first preferred embodiment of the invention, the cell adhesion protein is in porous macroscopically oriented form because this creates a scaffolding to which invading cells can adhere as described above. According to a second preferred embodiment of the invention, there is provided a depot formulation comprising a complex of fibronectin or a fragment thereof and Cu ions, a growth factor binding agent linked to the complex, and a growth factor bound to the binding agent. This allows a growth factor which promotes wound healing to be concentrated and released at the wound site.

Macroscopically oriented materials

The macroscopically oriented cell adhesion protein used in the first preferred embodiment of the invention comprises large scale aggregates of cell adhesion protein, which self-assemble under favourable conditions as fibrils, the molecules in each individual fibril lying substantially parallel to each other, each individual fibril being oriented over a distance of at least 100 μm and the fibrils being oriented substantially parallel to each other over macroscopic distances such as at least 0.1 mm, preferably 0.5 and most preferably at least 1 mm. Individual fibrils may show orientation over a considerable distance, for instance up to 0.5 mm, possibly up to 1 mm or even for 5 mm or more, for instance 1,2,3 or 5 cm. The aggregate of fibrils may be oriented for over 5 mm or 1 cm or more, for instance 2,3, or 5 cm and, when prepared as a continuous web for subsequent division into individual dressings, the aggregate may be oriented over distances of many centimeters or even many meters.

The fibrils may be oriented in a single direction and form a sheet or mat, possibly on a substrate for support, which may be applied to a wound. In more complex arrangements such sheets or mats may be laminated in non-parallel directions, for instance with the fibrils of one layer oriented at 90° to fibrils in a second layer. The fibrils may be arranged into fibres or may be formed on a substrate or oriented by fibres of a substrate, and such fibres may be formed into woven and non-woven webs having at least one and often two or more orientation directions. When the oriented materials are formed by coating on a substrate, preferably the substrate will be a biodegradable or resorbable material such that it may be left in the wound and will eventually be destroyed as the wound heals or once it has healed. Alternatively, the substrate may be a physical support which is removed after formation of the oriented material.

In use the complexes of the invention comprising a macroscopically oriented protein may be applied to wounds to direct and promote cell invasion and thereby to increase the strength, cosmetic acceptability, healing time or other desirable characteristic of the healed wound. By way of example a simple unidirectionally oriented mat may be used with the orientation direction across the width of a linear wound in order to promote the closing of the wound and enhance the resistance to re-opening of the wound. In another example, more complex webs having multiple orientation directions may be used to promote regrowth of damaged tendons and intervertebral discs whilst directing adoption by the invading cells of orientations matched to that of the surrounding undamaged tissue or to recreate orientations of the original damaged tissue. Thus the use of the oriented complexes of the invention will often involve aligning one or more orientation directions of the material with respect to features of the wound or surrounding tissues.

A particular application of the materials of the invention is in stimulation of new capillary growth, a frequently perceived objective for many forms of wound repair. Classically, the approach has been to attempt to stimulate angiogenesis, generally using a diffusible factor. However, one part of the process of angiogenesis is endothelial cell adhesion to and migration over the substrate matrix. A development of the present invention can be applied to this by promoting attachment/migration of capillary cells to discrete fibres or strands. These strands would be orientated in the direction of the required capillary growth. Strands can take the form of (i) pure fibronectin/Cu complex in macroscopic fibrous form; (ii) oriented fibronectin/Cu complex strands laid into wound implant materials (e.g. hyaluronan, gelatin or modified cellulose sponges); (iii) oriented fibronectin/Cu complex coated on braided resorbable sutures. Whether formed of oriented complex or coated with the complex, the individual strands should be less than 200 µm wide (ideally between 1 and 100 µm). These structures form excellent support and adhesion substrates for repair cells.

In a further modification (particularly of the complex-coated, braided suture) it is possible to incorporate a chemotactic stimulus by attaching a solid, growth factor containing gel to one end of the suture. A natural example of such a "gel" would be a blood or plasma clot (ideally prepared from the patient's own blood). Artificial substrates based on gelatin (or other gel-forming material) containing the required angiogenic factor could also be used. This suture would be drawn through or across the damaged tissue and left in position in such a way that new vessels would grow towards the end bearing the gel or clot. This form of suture may usefully be employed as an "angiogenic track" during repair of avascular or poorly vascular tissues such as torn menisci, ligaments or tendons.

Fibronectin may be obtained commercially in non-oriented form and may be oriented by processes such as are described below. The fibronectin may be recombinant or biochemically purified. Other cell adhesion proteins are well known in the literature; again these are available in non-oriented form and require processing for instance as described below.

The complex of the invention will usually be provided in sterile, pyrogen-free form.

Oriented complexes according to the invention may further comprise additional therapeutic agents, for instance additional cell adhesion proteins in soluble form (either the same or different from the base insoluble cell adhesion protein), agents which promote wound healing such as growth factors, growth hormones, and cytokines, clotting factors, platelet adhesion promoters such as thrombin, agents which promote calcification, collagen, fibrinogen, antimicrobial agents, heparin, growth factor binding proteins and proteoglycans. These agents may be cross-linked as soluble agents to the oriented cell adhesion protein by Cu ions (e.g. $Cu^{2+}$ ions).

The fibrils and oriented complexes may be used as formed or stabilised by cross-linking using chemical reagents such as glutaraldehyde or enzymes such as factor XIIIa, which is a transglutaminase. Cross-linking with other components such as collagen and fibrinogen, for instance using a transglutaminase, is also contemplated. Where the complexes of the invention include collagen and/or fibrinogen it is preferred for these also to be oriented substantially parallel to the fibrils of cell adhesion protein.

Preferably the oriented complexes of the invention are used as, or as part of, a wound dressing, or are applied to open wounds separately from a conventional dressing. To derive improved strength and/or cosmetic acceptability of the mature wound it is preferred that the oriented complexes are applied to the wound with the or an orientation direction aligned with features of the surrounding tissues so as to encourage invasion along the orientation direction. For instance, the fibres may be aligned with muscle fibres in the wound or underlying tissue, across a linear wound or parallel with or at right angles to directions in which a tissue will be strained once healed.

Macroscopically oriented cell adhesion proteins may be produced as described in WO-A-92/13003 by a process which comprises forming and orienting cell adhesion protein fibrils from solution and removing the solvent.

Depot formulations

The second preferred embodiment of the invention relates to the use of Cu complexes of fibronectin or a fragment thereof. The fibronectin or fragment acts as a targetting entity which assists in delivery of the depot formulation to wound tissue, especially when a cell-binding domain is included.

The growth factor binding agent is suitably a polysulphated polysaccharide such as heparin or heparan sulphate or a polypeptide such as BP53 which specifically binds a growth factor.

Heparin and heparan sulphate are well-known anticoagulants and are commercially available. BP53 is a polypeptide component of serum isolated by known techniques by column fractionation which initially affords a 150 kDA complex that may be dissociated at low pH to give BP53. BP53 may be used as such or in the form of a complex thereof, such as the 150 kDa complex.

Useful growth factors include fibroblast growth factor (FGF), epidermal growth factor (EGF), endothelial derived growth factor (EDGF), insulin-like growth factor I or II (IGF-I or IGF-II). BP53 is used to bind IGF; heparin and heparin sulphate bind a class of growth factors including FGF, EGF and EDGF.

Preferred depot formulations comprise fibronectin or a fragment thereof and the growth factor binding agent, especially heparin, in a weight ratio of 5:1 to 100:1, preferably from 20:1 to 50:1

Without wishing to be bound by this theory the present inventors believe that the growth factors bind to the binding agents such as heparin or BP53 and are effectively presented to cells in or surrounding a wound by the binding agent. By immobilising the binding agent on the fibronectin or fragment thereof, the wound healing promoting agents can be delivered to a wound site, stored there and presented and released to target cells in a prolonged or controlled manner or both to influence and enhance various aspects of wound healing. Moreover, the use of cell-binding domains of fibronectin allows the depot formulation to bind to tissues at or adjacent to the wound site and to be retained in place for the necessary period while wound healing is taking place.

A variety of means are available for linking binding agents such as heparin and BP53 to the fibronectin or fragment thereof. In general, chemical cross-linking using non-deleterious agents and conditions may link the binding agent to the fibronectin. A useful class of chemical cross-linking agents is the carbodiimides which are well known for conjugating materials such as these.

When fibronectin or a fragment thereof including the heparin binding domains is used, heparin or heparan sulphate may be bound via the non-covalent interaction with the heparin receptor in the heparin binding domain.

Alternatively the binding agent may be bound to the fibronectin or fragment thereof via a carrier material such as polylysine. In this case the fibronectin or fragment thereof and the binding agent are both bound by chemical cross-linking to the carrier material.

Combinations of these techniques may be used such that, for instance heparin or BP53 may be bound by chemical cross-linking to the fibronectin and to a carrier material which is itself cross-linked to the fibronectin. Alternatively, or in addition, heparin-binding domains of fibronectin may be used for non-covalent binding of heparin and heparan sulphate.

Since heparin and heparan sulphate molecules can each bind to more than one heparin binding domain of fibronectin, materials comprising fibronectin or heparin binding domains thereof linked to carriers such as polylysine will be aggregated by heparin or heparan sulphate and can be used to form paste-like formulations.

Preferred depot formulations comprise heparin-binding domains and heparin and are presented as pastes. Other preferred depot formulations comprise cell-binding domains of fibronectin which afford enhanced adhesion between the depot formulations and cells in or adjacent to the wound.

Another aspect the invention relates to materials for use in depot formulations as hereinbefore described which materials comprise a complex of fibronectin or a fragment thereof and Cu ions, and a growth factor binding agent, preferably a complex of fibronectin or a heparin binding domain fragment thereof and Cu ions, and heparin, heparan sulphate or BP53, bound to the complex.

These materials may be used to produce depot formulations by contact with a growth factor and capture thereof. This may be achieved by, for instance, perfusing the material with a solution of the agent. In a particularly preferred embodiment the material is perfused with a patient's blood or serum prior to an operation or surgical procedure in order to load the material with wound healing promoting agents from the patient's own circulation (thus avoiding the risks of exogenous blood products). The perfused material absorbs growth factors and can then be used as a depot formulation to aid recovery of the same patient from the operation or surgical procedure.

This mechanism may be exploited by placing the material at the site of the wound, where it will accumulate growth factors from the patient's serum and act as a depot formulation by presenting and releasing the agents to cells in the vicinity of the wound. In addition, depot formulations as previously described will accumulate and release growth factors from the patient's serum whilst releasing the initial growth factors included in the depot formulation prior to implantation, and will continue to do so after the initial growth factors have been consumed.

In yet another aspect of the invention, the depot formulations, or materials for use therein comprise porous macroscopically oriented complexes of Cu and fibronectin or fragments thereof as described above.

The oriented materials described in WO-A-92/13003 may be used as a carriers for the materials and depot formulations described above. In this case, the oriented materials may have Cu ions incorporated therein in addition to the Cu ions incorporated in the fibronectin of the depot formulations or materials for use therein. Furthermore, the fibronectin in the depot formulations and materials for use therein may itself be in the form of porous macroscopically oriented wound treatment material.

Uses of the Complex

The present invention further provides complexes, depot formulations or materials for producing depot formulations as hereinbefore defined for use in a method of surgery or therapy practised on the human or animal body. The invention also provides the use of a complex, depot formulation or material for producing depot formulations as hereinbefore defined in the manufacture of a medicament, dressing or device for use in a method of surgery or therapy practised on the human or animal body. In particular aspects the methods of surgery or therapy involve promoting wound healing or improving the appearance or strength of a healed wound or any combination thereof. The method of surgery or therapy may alternatively involve the growth of autograft material, such as skin or ligament, promoted by the complexes, depot formulations or materials of the invention. When porous macroscopically oriented materials described above are used such growth may be directed by the oriented materials. The invention further provides a method of treatment of a wounded human or animal comprising applying to the wound an effective, non-toxic amount of a complex, depot formulation or material for producing a depot formulation as hereinbefore defined.

The types of wound which may be treated include wounds to the skin and ocular tissues (including burns), surgical flaps, wounds to nerves and wounds to blood vessels. A complex, depot formulation or material for producing a depot formulation may be used to promote regrowth of a damaged nerve by employing the complex, depot formulation or material in a long-lasting graft. The complex, depot formulation or material are used in amounts sufficient to promote wound healing. The exact amount used will ultimately be at the discretion of the physician but, for example, 0.1 to 10 mg of call adhesion protein in the complex, depot formulation or material may be used per cm$^2$ of wound area.

The depot formulations and materials for use therein (optionally comprising a porous macroscopically oriented cell adhesion protein) may be supported on a substrate. Preferably, the substrate is a biodegradable or resorbable material such that it may be left in the wound and will eventually be destroyed as the wound heals or once it has healed.

Processes for making the Complex

The invention includes a method of preparing a complex comprising a cell adhesion protein or a fragment thereof and Cu ions, which method comprises contacting the protein or fragment thereof with a solution comprising Cu ions. It is usually convenient to treat the cell adhesion protein with the Cu solution while the protein is in insoluble form, for instance in the form of a macroscopically oriented material. However it is also possible to treat the protein in solution and then precipitate the protein once the Cu ions have been incorporated or to treat the protein solution with Cu ions at the same time as precipitating it from solution. An additional therapeutic agent in soluble form may be cross-linked to an insoluble cell adhesion protein by mixing the therapeutic agent and protein in the presence of Cu ions.

The protein or fragment is generally contacted with the Cu solution for a period of at least 1 hour, for example from 1 to 4 hours, and then excess Cu solution is washed away. The temperature at which the protein or fragment is contacted with the Cu solution depends on factors such as the nature of the aggregate of the protein or fragments and the solvent, but is suitably from −5° to 50° C., preferably 10° to 37° C. During this period the mixture is preferably agitated, for example by roller mixing. A preferred method of preparing the complex comprises (i) mixing a solution comprising Cu ions and aggregated cell adhesion protein;

(ii) agitating the mixture for at least 1 hour at from 10° to 37° C.; and (iii) washing away excess solution.

A range of types of copper-containing compound can be used to treat the mats. Examples of suitable copper ion-containing solutions are copper (I) chloride, copper (II) chloride, copper acetate and copper sulphate solutions.

The concentration of Cu ions in the Cu solution is suitably from 60 µM to 60 mM, preferably 0.15 mM to 3.0 mM. At the higher range of copper loading (i.e. 0.6 mM to 60 mM), copper toxicity occurs and this may prove useful for local delivery of copper in cytotoxic therapy to reduce the growth of granulation tissue (copper sulphate is used directly for this purpose at present). The lower range of copper loading (i.e. 60 µM to 600 µM) may be useful for other purposes such as promoting cell growth.

Excess Cu solution is suitably washed away with phosphate buffered saline (pH 7.5), tris-HCl buffered saline (pH 7.5) or distilled water.

Using the method described above, Cu ions are taken up avidly into cell adhesion proteins such as fibronectin and fragments thereof. The amount of Cu incorporated can be determined by trypsin digestion of the protein or fragment and measuring the amount of Cu released by atomic absorption spectorscopy. The amount of Cu incorporated is dependent on the concentration of Cu ions in the solution contacted with the protein or fragment, but is typically from 1 to 100 µg of Cu/mg protein, for example from 9 to 29 µg/mg when the concentration of Cu ions in the solution is from 0.15 to 3 mM.

When it is wished to prepare a depot formulation or a material for producing a depot formulation, the Cu ions may be incorporated into the preformed depot formulation or material. Alternatively, the Cu ions may first be incorporated into the fibronectin or fragment and the resulting complex used to form the depot or material.

EXAMPLES

The following Examples serve to illustrate the invention.

BRIEF DESCRIPTION OF THE DRAWINGS

FIG. 3 shows the incorporation of copper from solutions of four different copper compounds relative to the protein content of each fibronectin (Fn) mat.

EXAMPLE 1

1. Fibronectin mats (Fn mats) (approx. 1 mg dry weight) were treated with copper sulphate in water (250 µl, 6.25 mM) and mixed gently for 3 h at 37° C.
2. Additional mats were incubated as described in 1 but for a total of 18 h.
3. At the end of incubation the mats were washed 5 times with phosphate buffered saline (PBS) (pH 7.5), each was being with 2 ml PBS for 10 min with mixing.
4. The washed mats were incubated for 15 h at 22° C. with PBS (1 ml). The supernatants from all stags were removed for protein and copper analysis.
5. The final pellet (Fn mat) was digested by incubation with trypsin (total of 60 µl/ml) at 37° C. for 1 hr. Solublised pellets were assayed for protein by the Bradford Assay (Bradford M. A rapid and sensitive method for the measurement of microgram quantities of protein utilising the principles of dye-binding Anal. Biochem (1976) 72: 248–254).
6. Control mats were treated in the same way as in steps 1 to 5 but with sodium acetate buffer pH 5.5 (250 µl) or the copper carrier protein cerulplasmin (250 µl 10 mg/ml in PBS).

Figure 1A:
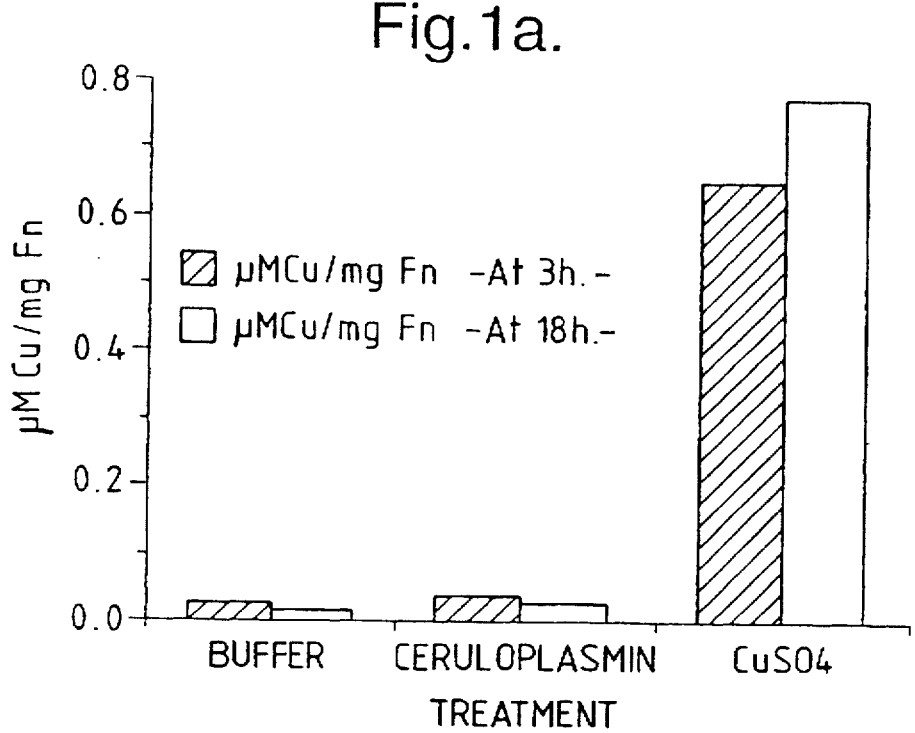
FIG. 1a shows the mean incorporation of $Cu^{2+}$ ions into fibronectin mats over 3 and 18 h incorporation times from solutions of copper sulphate and ceruloplasmin, and from buffer.

FIG. 1a shows the mean incorporation of copper under these conditions into Fn mats over 3 and 18 h incorporation times, from solutions of copper sulphate and ceruloplasmin. The copper content of the buffer treated mats was below the level of assay sensitivity. Ceruloplasmin treatment left trace levels of copper whilst copper sulphate treated mats were blue with incorporated copper. Only a small improvement in binding was produced by the longer incubation time (41 to 49 μgCu/mgFn).

Figure 1B:
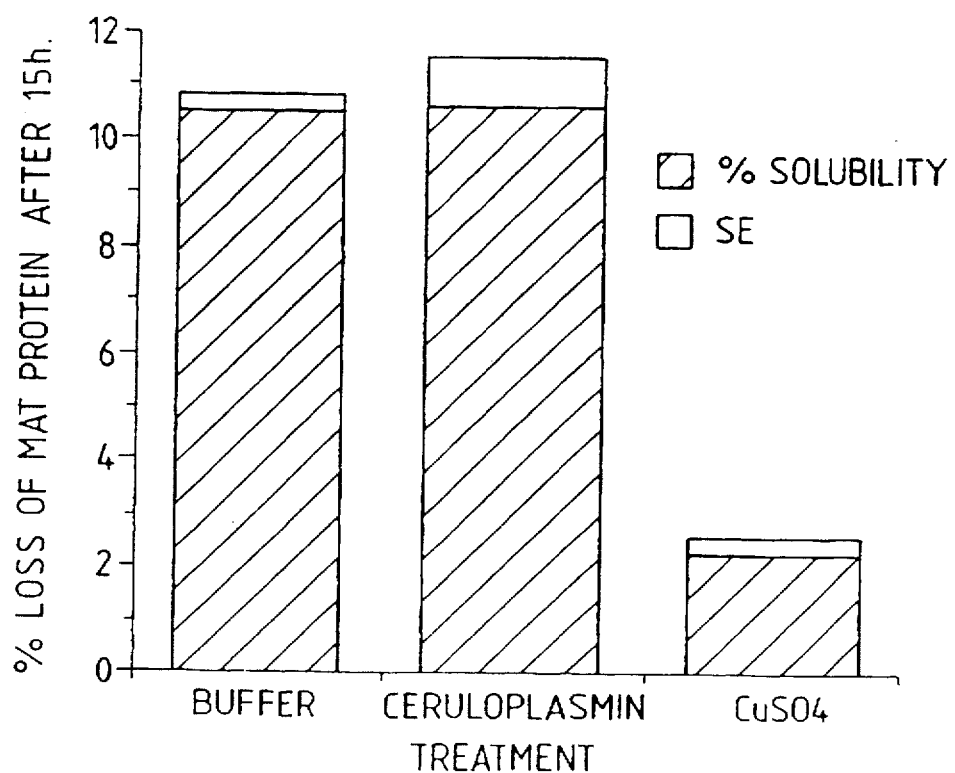
FIG. 1b shows the % release of protein from fibronectin mats treated with copper sulphate, ceruloplasmin and buffer over a 15 h incubation in phosphate buffered saline (PBS) at 37° C.

Under these conditions (notably the small volume of copper sulphate used to treat the mats) most of the available copper was bound to the mats. FIG. 1b shows the release of protein from copper-treated and control mats over a 15 h incubation at 37° C. in PBS. Clearly, loss of protein from the mat (i.e. breakdown) was greatly reduced by $Cu^{2+}$ incorporation. This indicates that copper-treated mats were 5 fold more stable (i.e. gave approx 20% of the protein loss of control mats) than untreated controls.

EXAMPLE 2

1. Fn mats (approx 2 to 3 mg dry weight) were roller mixed (37° C., 4 h) with copper sulphate solutions (1 ml, ranging from 0 to 0.5 mg/ml).
2. Unbound copper sulphate solution was removed by spinning down the Fn mat pellet and decanting off the supernatant.
3. The treated mat was washed by roller mixing (20 h) in PBS (1 ml) and again the supernatant was recovered for analysis.
4. Mats were then solublised (as in item 5 of Example 1 above) by trypsin digestion (1 h at 37° C. into 1 ml).
5. Supernatants and solubilised Fn mats were analysed for total protein and copper as in Example 1.

Figure 2A:
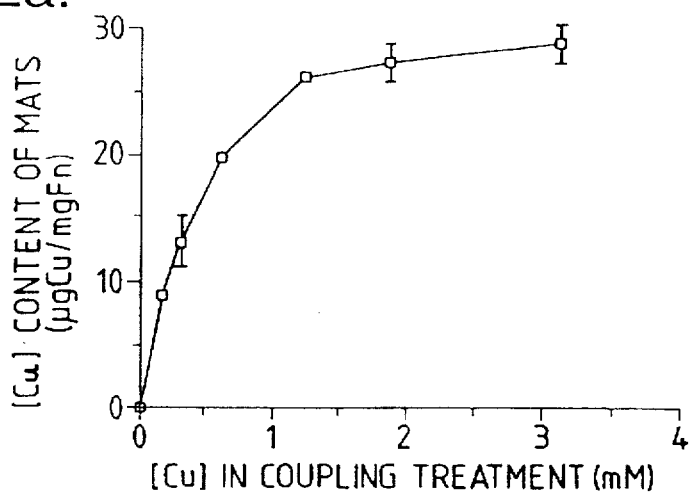
FIG. 2a shows the relationship between the concentration of $Cu^{2+}$ solution used to treat fibronectin mats and the amount of $Cu^{2+}$ taken up by the mats. Each point is the mean of a duplicate and the standard deviation is shown where it was great enough to plot.
Figure 2B:
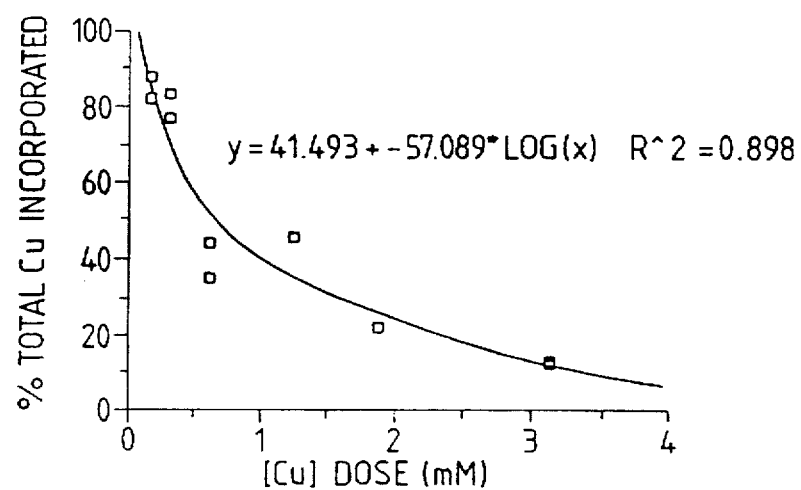
FIG. 2b shows the relationship between the concentration of $Cu^{2+}$ solution used to treat fibronectin mats and the % $Cu^{2+}$ removed from the solution by the mats.

FIG. 2a shows the dose dependent manner in which copper was taken up by Fn mats under these conditions. Incorporation of copper in Fn-mats was logrithmically related to the loading concentration of $Cu^{2+}$ (as copper sulphate) at the copper treatment stage. The degree of utilisation, or uptake of $Cu^{2+}$ from the coupling reaction mixture mirrored this (FIG. 2b), such that percentage incorporation of $Cu^{2+}$ was also related to the loading $Cu^{2+}$ concentration in a loganithimic manner. It is notable that at lower doses of $Cu^{2+}$ the Fn mats were able to chelate over 80% of the available metal ions.

Figure 2C:
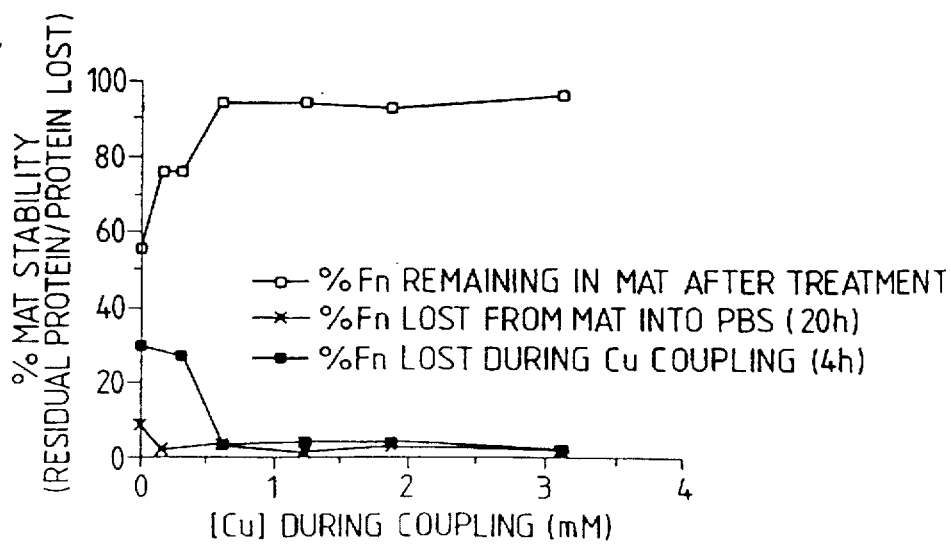
FIG. 2c shows the effect of increasing the $Cu^{2+}$ content of fibronectin mats on the stability of the mats, as measured by the % release of fibronectin over a 20 h incubation in PBS and the % total protein remaining in the mats after the incubation, in relation to the concentration of $Cu^{2+}$ solution used to treat the mats.

The effect of increasing the copper content on mat stability is shown in FIG. 2c. Over the coupling range of $Cu^{2+}$ (0 to 3.125 mM $Cu^{2+}$) used above, there was a dramatic increase in mat stability with increasing $Cu^{2+}$ concentration. This was evident both as a fall in the release of Fn (over 20 h to PBS) and as an increase in the total protein remaining in the mat at the end of the experiment. This stability reached its optimum (plateau) between 0.3 and 0.6 mM and was thereafter unchanged despite increased $Cu^{2+}$ content.

EXAMPLE 3

Polyacrylamide gel electrophoretic analysis of tryptic fragments: comparison with and without $Cu^{2+}$ treatment SDS polyacrylamide gel electrophoretic (SDS PAGE) analysis of peptide mats was used to assess the nature and level of cross-linking of mats by $Cu^{2+}$, incorporation.
1. Fn mats were treated with copper sulphate as in the preceding Examples.
2. The $Cu^{2+}$ treated mats were digested with trypsin (200 mg/ml) in PBS at 37° C. in parallel with copper $Cu^{2+}$ free mats. The total digest time was the same for all mats.
3. Peptide maps of Fn fragments generated by the treatment were analysed by SDS PAGE (Laemmli UK Cleavage of structural proteins during the assembly of the head of bacteriophage T4. Nature (1970) 227: 680–85). The analysis was carried out under reducing and non-reducing conditions (denaturation at 100° C., 2 min with or without 20 mM dithiothreitol). Bands were visualised by routine coomassie blue staining.

Comparison of peptide maps indicated that $Cu^{2+}$-treated and $Cu^{2+}$-free mats produced a range of fragments of similar molecular weight. This indicates that large scale Fn-Fn intermolecular cross-linking was reversible and noncovalent in nature. There were indications of differences in band patterns, consistent with the idea that a few, highly specific, stable bonds are formed. In some cases, prereduction of samples indicated that these bonds were disulphide in nature.

EXAMPLE 4

Use of alternative copper compounds

A variety of copper-containing compounds were compared to test the importance of the counter-ion to the incorporation.

Similar sized pieces of Fn-mats were prepared in triplicate. Test solutions of COPPER (I) CHLORIDE, COPPER (II) CHLORIDE, COPPER ACETATE and COPPER SULPHATE were prepared at 1.56 mM in distilled water. Each mat was placed into 1 ml of the test solution, and incubated at 37° C. for 4 hours with regular mixing. At the end of the time period supernatants were decanted off the mats which were then washed exhaustively in phosphate buffered saline to remove unbound copper reagent.

The washed mats were solubilised for total protein assay (Bradford, Coomassie Blue Dye-binding technique) and for total copper by standard atomic absorption assay.

FIG. 3 shows the incorporation of copper from each solution, relative to the protein content of each mat. There was no difference detected between the incorporation of copper for different test solutions indicating that the counter ions used have no significant influence. This suggests that a range of types of copper-containing compound could be used to treat the mats.

EXAMPLE 5

Copper toxicity of Fn-mats treated with high levels of copper

Copper treated Fn-mats were prepared as before using initial loading levels of 25,50,100,200,300 and 500 μg/ml of copper sulphate. After incubation and washing to remove unincorporated copper, the mats were dried and sterilised by gamma irradiation. Each mat was attached to a culture dish, seeded with $1 \times 10^5$ human dermal fibroblasts and monitored for morphological changes over a 7 day time period. Changes in cells on the Fn-mats were not visible in this system by phase contrast microscopy, due to the density of the material. Assessments were based on the cells adherent to the plastic.

Over the first 48 hours there was little sign of cell death (i.e. no cell detachment from the plastic). In the two highest copper concentrations, however, there were some morphological changes in the adherent cells. Cells become large and flattened with a granular cytoplasm and long, thin, disintegrating processes. This was most pronounced in cells adjacent to the mat and decreased towards the edges of the dish, consistent with the idea that toxicity was due to leaching of copper from the mats. After 120 hours there was 40–60% cell detachment from the dishes, due to cell death, in concentrations over 200 μg/ml. At this stage the approx % cell viability was estimated by addition of the vital stain neutral red.

| Initial Copper conc. Treatment | % adherent cell viability |
| --- | --- |
| 0 (control) | 100% |
| 25 µg/ml | 90% |
| 50 | 85% |
| 100 | 65% |
| 200 | 50% |
| 300 | 25% |
| 500 | 15% |

This indicates that high levels of copper incorporation will produce toxic effects in cultured fibroblasts as the metal ion is lost from the Fn-mats. Loss of cell viability, over 120 days, was insubstantial at copper coupling levels below 100 µg/ml. However, at levels of 300 to 500 µg/ml, copper sulphate toxicity was marked.

At the higher range of copper loading the mats may prove useful as local delivery materials for copper to act as a cytotoxic therapy to reduce the growth of granulation tissue (copper sulphate can be used directly for this purpose at present).

I claim:

1. A stable complex comprising a porous macroscopically oriented mat of fibronectin or a fragment thereof and Cu ions.

2. A complex according to claim 1 in which the Cu ions are $Cu^{2+}$ ions.

3. A wound dressing comprising a stable complex as claimed in claim 1.

4. A method of preparing a stable complex comprising a porous macroscopically oriented mat of fibronectin or a fragment thereof and Cu ions, which method comprises contacting the mat of fibronectin with a solution comprising Cu ions.

5. A method according to claim 4 in which the Cu ions are $Cu^{2+}$ ions.

6. A method of treating a wound comprising applying to the wound an effective, non-toxic amount of a stable complex as claimed in claim 1.

7. A method of promoting regrowth of a damaged nerve, which method comprises applying thereto an effective, non-toxic amount of a stable complex as claimed in claim 1.

8. A method according to claim 7 wherein the stable complex is employed in a long-lasting graft.

9. A method according to claim 7 wherein the nerve regrowth is directional.

10. A complex according to claim 1 which comprises from 1 to 100 µg of Cu per mg of fibronectin.

11. A complex according to claim 10 which comprises from 9 to 29 µg of Cu per mg of fibronectin.

12. A method according to claim 4 wherein the solution comprising Cu ions is selected from the group consisting of copper (I) chloride, copper (II) chloride, copper acetate and copper sulphate solutions.

13. A method according to claim 4 wherein the concentration of Cu ions in the solution is from 60 µg to 60 mM.

* * * * *